US00PP15500P2

(12) United States Plant Patent
Meilland

(10) Patent No.: US PP15,500 P2
(45) Date of Patent: Jan. 25, 2005

(54) MINIATURE ROSE PLANT NAMED 'MEIMIROS'

(50) Latin Name: *Rosa hybrida*
Varietal Denomination: Meimiros

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 21 days.

(21) Appl. No.: 10/726,616

(22) Filed: Dec. 4, 2003

(51) Int. Cl.[7] ..... A01H 5/00
(52) U.S. Cl. ..... Plt./120

(58) Field of Search ..... Plt./120, 121, 127, Plt./128

*Primary Examiner*—Anne Marie Grunberg
*Assistant Examiner*—June Hwu
(74) *Attorney, Agent, or Firm*—Burns, Doane, Swecker & Mathis, L.L.P.

(57) ABSTRACT

A new and distinct variety of rose plant of the Miniature Class is provided which abundantly forms on a nearly continuous basis attractive very double bright Coral Salmon Pink blossoms that well retain their coloration upon maturity. The growth habit is spreading-upright bushy. Very dense dark green semi-glossy foliage is formed that contrasts nicely with the blossom coloration. Plants of the new variety develop well following the rooting of cuttings. The new variety is well suited for pot forcing under greenhouse growing conditions to form a distinctive gift plant.

1 Drawing Sheet

Figure 1:
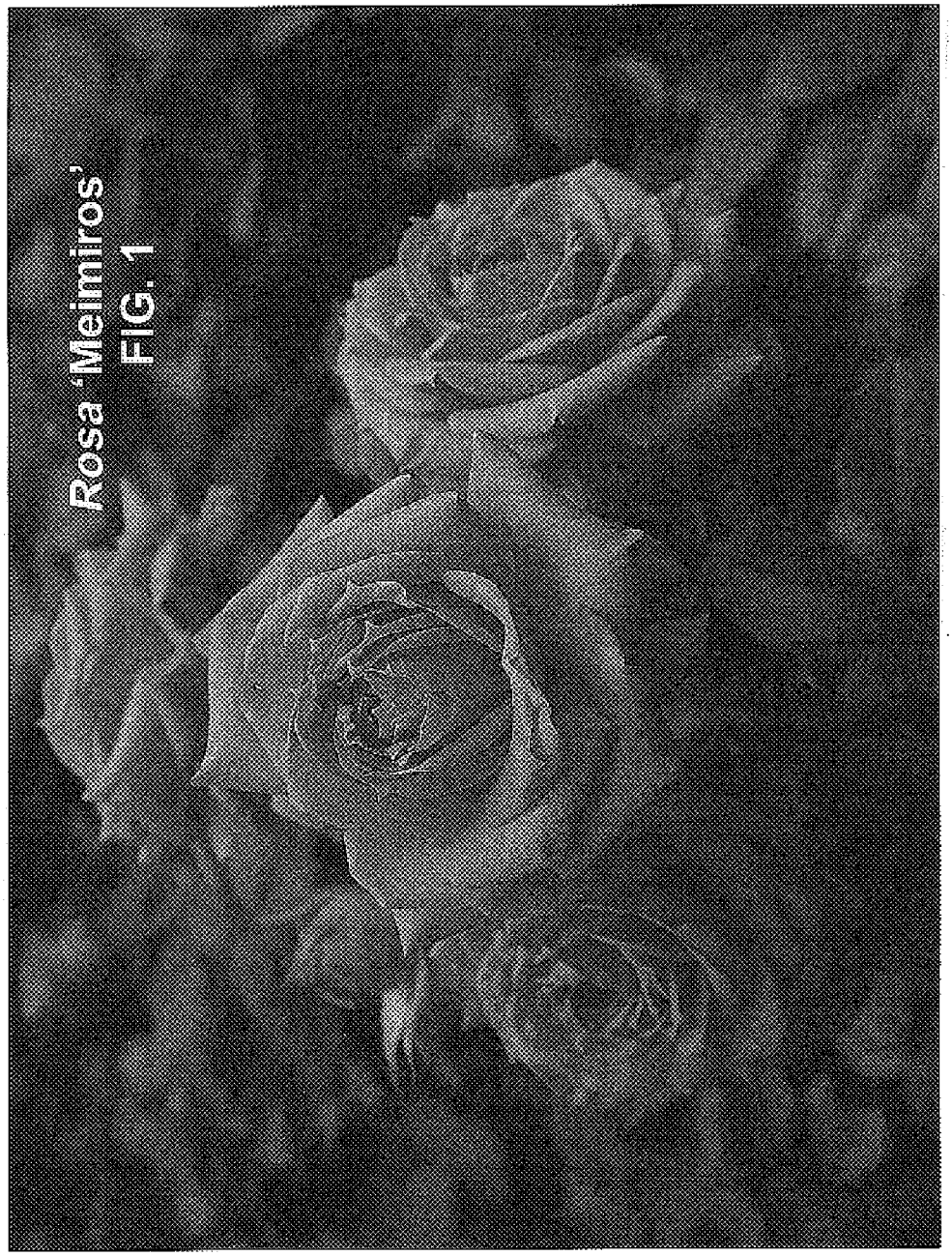

Botanical/commercial classification: *Rosa hybrida*/Miniature Rose Plant.
Varietal denomination: cv. 'Meimiros'.

SUMMARY OF THE INVENTION

The new variety of *Rosa hybrida* Miniature rose plant was created by artificial pollination wherein two parents were crossed which previously had been studied in the hope that they would contribute the desired characteristics. The female parent (i.e., the seed parent) of the new variety was the product of the cross of the 'Meichanso' variety (non-patented in the United States) and the 'Meishasen' variety (non-patented in the United States). The 'Meichanso' variety sometimes is known as the 'Parador' variety. The male parent (i.e., the pollen parent) was the 'Meifinaro' variety (U.S. Plant Pat. No. 5,180). The 'Meifinaro' variety has been marketed under the AMERICAN INDEPENDENCE trademark. The parentage of the new variety can be summarized as follows:

('Meichanso'×'Meishasen')×'Meifinaro'.

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) exhibits a spreading-upright bushy growth habit,
(b) forms in abundance on a nearly continuous basis attractive very double bright Coral Salmon Pink blossoms that well retain their coloration upon maturity,
(c) forms very dense dark green semi-glossy foliage,
(d) develops well following the rooting of cuttings, and
(e) is well suited for pot forcing under greenhouse growing conditions.

The new variety well meets the needs of the horticultural industry. It is particularly well suited for pot forcing under greenhouse growing conditions to form a distinctive gift plant.

The new variety can be readily distinguished from its parental varieties. More specifically, the 'Meichanso' variety forms significantly larger blossoms that are Geranium Red in coloration, and the 'Meifinaro' variety forms smaller blossoms that initially are Neyron Pink in coloration and fade to nearly white at the time of petal drop. The new variety additionally can be distinguished from other previously known Miniature rose varieties in view of its distinctive blossom coloration combined with the display of an usually large number of petals.

The new variety has been found to undergo asexual propagation at West Grove, Pa. by a number of routes, including budding, grafting, and the use of cuttings. Asexual propagation by the above-mentioned methods as performed in Pennsylvania has shown that the characteristics of the new variety are strictly transmissible from one generation to another. Good plant development is displayed regardless of the mode of asexual propagation.

The new variety has been named the 'Meimiros' variety.

BRIEF DESCRIPTION OF THE PHOTOGRAPH

The accompanying photograph shows as nearly true as it is reasonably possible to make the same, in a color illustration of this character, a typical specimen of the new variety. The rose plant of the new variety was three years of age and was photographed during October 2003 while growing on their own roots in a greenhouse at West Grove, Pa.

FIG. 1—illustrates a specimen of a typical flower cluster with accompanying foliage.

DETAILED DESCRIPTION

The chart used in the identification of the colors is that of The Royal Horticultural Society (R.H.S. Colour Chart). The description is based on the observation of three year-old specimens of the new variety which were observed during October 2003 while growing on their own roots in greenhouses at West Grove, Pa.

Class: Miniature.

Plant:

*Height.*—Approximately 60 to 65 cm on average at the end of the growing season.

*Width.*—Approximately 65 to 70 cm on average at the end of the growing season.

*Habit.*—Spreading-upright bushy.

Branches:

*Color.*—Young stems: glabrous and near Green Group 137C. Adult wood: glabrous and near Green Group 137C.

*Thorns.*—Immature thorns: possess an elliptical base, taper to a sharp point at the apex, measure approximately 5 mm in length and approximately 2 mm in width at the base, and are Yellow-Green Group 153A in coloration. Mature thorns: possess an elliptical base, taper to a sharp point at the apex, measure approximately 6 mm in length and approximately 3 mm in width at the base, and are Yellow-Green Group 153A in coloration.

Leaves:

*Petioles.*—Upper surface: bear scattered hairs and stiff glandular hairs, and near Green Group 143A in coloration. Under surface: typically bear a few minute to small minor prickles and occasional stiff glandular hairs, and near Green Group 143A in coloration.

*Leaflets.*—Number: 3, 5 (most often), and 7. Shape: typically broadly elliptical to elliptical to ovate to occasionally narrowly ovate. Apex: acute to broadly acute to abruptly acuminate. Base: broadly rounded to broadly cuneate to cuneate. Texture: substantially glabrous on the upper surface and glabrous on the lower surface, and somewhat papery. Margin: serrulate. General appearance: very dense, dark green, and semi-glossy. Leaf size: varies widely within and between leaves of varying leaflet numbers with the overall leaf lengths commonly being approximately 6 to 10.5 cm and the overall leaf widths commonly being approximately 5 to 7.5 cm. For a three-leaflet leaf a typical length commonly is approximately 6 to 8 cm and a typical width commonly is approximately 5 to 7 cm. For a five-leaflet leaf a typical length commonly is approximately 7.5 to 10.5 cm and a typical width commonly is approximately 5.5 to 7.5 cm. For a seven-leaflet leaf a typical length commonly is approximately 8 to 10 cm and a typical width commonly is approximately 5.5 to 7.5 cm. Color (adult foliage): Upper surface: near Green Group 139A. Under surface: near Greyed-Green Group 191A. Petiole: approximately 12 mm in length and approximately 3 mm in diameter.

Inflorescence:

*Number of flowers.*—Commonly approximately 1 to 4 per stem.

*Peduncle.*—Near Green Group 143C in coloration, occasionally with simple trichomes, the length commonly is approximately 3.6 to 5 cm, and the diameter commonly is approximately 1.9 mm.

*Sepals.*—Five in number, lanceolate, possess an apex that is acutus, approximately 20 mm in length, approximately 6 mm in width at the widest point, Yellow-Green Group 144A in coloration on both surfaces, and with some foliaceous extensions.

*Buds.*—Shape: ovoid, approximately 22 mm in length, approximately 8 mm in diameter, and Yellow-Green Group 144A in coloration.

*Flower.*—Form: very double, and flat cup-shaped. Diameter: approximately 4 to 5 cm on average when fully open. Color when blooming and nearly fully open: Upper surface: near Red Group 48D and Red Group 49A and lightening towards and through Red Group 49B and 49C. Under surface: near Red Group 49A and lightening towards and through Red Group 49B and 49C, and with some areas of near Red Group 48D at upper petal areas. Color at full maturity: Upper surface: typically near Red Group 55B and lightening smoothly and continuously through Red Group 55C and 55D with a small area of near to White Group 155B and 155C near the base and towards the center as well as a small amount of near Green-White Group 157A at the petal base. Under surface: typically near Red Group 55B and lightening smoothly and continuously through Red Group 55C and 55D, and Red Group 56A and 56B. Stability of coloration: very good with coloration commonly being well maintained upon full maturity. Petal configuration: larger broad petals are found in the outside rows with the innermost petals commonly being narrower and distinctly folded over and crinkled. Petal number: ranges widely from approximately 65 to 110 under typical growing conditions. Petal texture: glabrous, membranaceous, relatively thin, and semi-translucent. Petal arrangement: rosulate. Petal shape: broadly obovate to obovate to narrowly obovate. Petal margin: entire though tends to be revolute and typically more towards the tip especially as the flower ages. Petal apex: typically abruptly acuminate and occasionally broadly rounded. Petal base: very broadly cuneate to narrowly cuneate. Petal size: on the outside commonly approximately 22 to 27 mm (average approximately 24 mm) in length and approximately 20 to 30 mm (average approximately 23 mm) in width, and on the inside commonly approximately 15 to 23 mm (average approximately 20 mm) in length and approximately 9 to 19 mm (average approximately 15 mm) in width. Petaloids: commonly approximately 8 to 15 per flower, commonly irregular in shape, approximately 8 mm×4 mm in size, and near White Group 155D with edges of Red Group 52D in coloration. Fragrance: none. Stamen number: commonly approximately 48 to 60. Filaments: commonly approximately 5 mm in length, and near Yellow-Orange Group 18A in coloration. Anthers: Yellow-Orange Group 22A in coloration. Pollen: present in an abundant quantity and near Yellow-Orange Group 23A in coloration. Pistil number: approximately 96 on average. Styles: commonly approximately 4 mm in length, and near White Group 155D at the base and changing to near Red Group 46A near the stigma. Stigma: Yellow-Orange Group 23A in coloration. Lasting quality: is influenced by environmental conditions with blooms commonly lasting approximately 7 days on the plant, and approximately 5 days when cut and placed in a vase.

Development:

*Vegetation.*—Vigorous.

*Blooming.*—Very abundant and nearly continuous under greenhouse growing conditions.

*Aptitude to bear fruit.*—None observed.

I claim:

1. A new and distinct variety of Miniature rose plant characterized by the following combination of characteristics:

(a) exhibits a spreading-upright bushy growth habit, (b) forms in abundance on a nearly continuous basis attractive very double bright Coral Salmon Pink blossoms that well retain their coloration upon maturity, (c) forms very dense dark green semi-glossy foliage, (d) develops well following the rooting of cuttings, and (e) is well suited for pot forcing under greenhouse growing conditions;

substantially as herein shown and described.

* * * * *

*Rosa* 'Meiniros'